United States Patent
Auner et al.

(10) Patent No.: US 9,207,122 B2
(45) Date of Patent: Dec. 8, 2015

(54) FOURIER-TRANSFORM INTERFEROMETER WITH STAIRCASE REFLECTIVE ELEMENT

(71) Applicant: Wayne State University, Detroit, MI (US)

(72) Inventors: Gregory Auner, Livonia, MI (US); Changhe Huang, Novi, MI (US); Christopher M. Thrush, Shelby Township, MI (US); Michelle A. Brusatori, Sterling Heights, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/373,132

(22) PCT Filed: Jan. 31, 2013

(86) PCT No.: PCT/US2013/024140
§ 371 (c)(1),
(2) Date: Jul. 18, 2014

(87) PCT Pub. No.: WO2013/116516
PCT Pub. Date: Aug. 8, 2013

(65) Prior Publication Data
US 2015/0029504 A1    Jan. 29, 2015

Related U.S. Application Data

(60) Provisional application No. 61/594,465, filed on Feb. 3, 2012.

(51) Int. Cl.
| | |
|---|---|
| *G01J 3/28* | (2006.01) |
| *G01J 3/44* | (2006.01) |
| *G01N 21/65* | (2006.01) |
| *G01J 3/18* | (2006.01) |
| *G01J 3/36* | (2006.01) |
| *G01J 3/453* | (2006.01) |
| *G01J 3/02* | (2006.01) |
| *G02B 5/18* | (2006.01) |
| *G02B 5/20* | (2006.01) |

(52) U.S. Cl.
CPC ............. *G01J 3/44* (2013.01); *G01J 3/0208* (2013.01); *G01J 3/0272* (2013.01); *G01J 3/18* (2013.01);
(Continued)

(58) Field of Classification Search
CPC ............... G01J 3/02; G01J 3/18; G01J 3/28; G01J 3/2803; G01J 3/2823
USPC .................................................. 356/300–334
See application file for complete search history.

(56) References Cited

U.S. PATENT DOCUMENTS

| | | |
|---|---|---|
| 4,999,234 A | 3/1991 | Cowan |
| 5,828,492 A | 10/1998 | Moser et al. |

(Continued)

FOREIGN PATENT DOCUMENTS

JP    2006-267388 A    10/2006

OTHER PUBLICATIONS

International Search Report and Written Opinion for related application No. PCT/US2013/024140, Mailing Date May 15, 2013, 7pp.

*Primary Examiner* — Abdullahi Nur
(74) *Attorney, Agent, or Firm* — Brinks Gilson & Lione

(57) ABSTRACT

An apparatus for performing Raman spectral analysis of a sample is described, comprising a coherent light source, an first optical chain to direct the coherent light to impinge on the sample, a second optical chain to direct the scattered light onto a diffraction grating, and a third optical chain to direct the diffracted light onto detection array. The diffraction grating is a plurality of alternating-slope stairsteps, wherein the portion of the step disposed parallel to the base of the diffraction grating is disposed so as to be orthogonal to the path of the scattered light from the second optical chain. The zeroth-order fringe is selected by a slit and directed onto camera. The resultant interferogram is Fourier transformed to produce a representation of the Raman spectrum.

14 Claims, 9 Drawing Sheets

(52) U.S. Cl.
CPC ............... *G01J 3/36* (2013.01); *G01J 3/4531* (2013.01); *G01N 21/65* (2013.01); *G02B 5/1861* (2013.01); *G02B 5/20* (2013.01)

(56) References Cited

U.S. PATENT DOCUMENTS

| | | | |
|---|---|---|---|
| 6,016,199 A | 1/2000 | Newton | |
| 6,084,710 A * | 7/2000 | Katsuma | 359/569 |
| 6,118,518 A * | 9/2000 | Hobbs | 356/4.09 |
| 6,268,921 B1 | 7/2001 | Seitz et al. | |
| 6,278,548 B1 | 8/2001 | Shimano et al. | |
| 6,449,237 B1 | 9/2002 | Yoo et al. | |
| 7,050,171 B1 | 5/2006 | Banerjee et al. | |
| 7,330,266 B2 | 2/2008 | Guerineau et al. | |
| 7,359,058 B2 | 4/2008 | Kranz et al. | |
| 7,466,421 B2 | 12/2008 | Weitzel | |
| 2005/0213472 A1 | 9/2005 | Ikenaka et al. | |

* cited by examiner

FOURIER-TRANSFORM INTERFEROMETER WITH STAIRCASE REFLECTIVE ELEMENT

The research in this application was sponsored in part by the U.S. Government under DOD TARDEC contracts W56HZV-06-C-0581 and W56HZX-09-C-0231 and which has rights in this invention.

TECHNICAL FIELD

This application relates to an apparatus for measuring optical spectra.

BACKGROUND

Optical spectrometry may be performed by a variety of techniques, including multiplex filtering, interferometers and dispersive optical devices. Spectrometers may include, for example, grating-based spectrometers, scanning Fourier transform spectrometers, and dispersive Fourier spectrometers. Grating-based spectrometers typically combine a number of bulk optics components including mirrors, lenses, gratings, optical gratings, apertures, and beamsplitters. Fourier transform spectroscopic technologies are often implemented by using a variant on a Michelson interferometer, with one of the mirrors being scanned in distance along an optical path. The resultant interferogram at the detector is the Fourier transform of the optical spectrum, and the optical spectrum may be recovered by performing a Fourier transform of the received time series of optical intensity data.

Amongst the practical applications of these techniques is Raman spectroscopy. When light is scattered from a molecule or crystal most photons are elastically scattered, having the same energy (frequency) and therefore, the same wavelength, as the incident photons. However, a small component (approximately 1 in $10^7$ photons) is inelastically scattered, at wavelengths that are shifted from the incident radiation. The inelastically scattered photons provide chemical and structural information that is uniquely characteristic of the substance being irradiated. High-resolution detection of this Raman-scattered energy normally requires extensive laboratory facilities and large spectrometer systems, which act as either monocronometers or interferometers. Such devices are generally not suitable for portable applications, being precision optical instruments and having moving or adjustable components.

Herein, the terms frequency and wavelength are used to describe the spectral characteristics of an energy spectrum, and a person of skill in the art will recognize that they are equivalent representations that are inversely proportional to each other, where the constant of proportionality is the speed of light. The terms will often be used somewhat interchangeably, so as to permit comparison with various conventional representations of bandwidth, resolution, and the like.

Raman spectra are typically expressed in wave numbers, which have units of inverse length. In order to convert between spectral wavelength and wave numbers of shift in the Raman spectrum, the following formula can be used:

$$\Delta w \left( \frac{1}{\lambda_0} - \frac{1}{\lambda_1} \right),$$

where $\Delta w$ is the Raman shift expressed in wave number, $\lambda_0$ is the excitation wavelength, and $\lambda_1$ is the Raman spectrum wavelength. Most commonly, the units chosen for expressing wave number in Raman spectra is inverse centimeters ($cm^{-1}$). Since wavelength is often expressed in units of nanometers (nm), the formula above can scale for this units conversion explicitly, giving $$\Delta w (cm^{-1}) = \left( \frac{1}{\lambda_0(nm)} - \frac{1}{\lambda_1(nm)} \right) \times 10^7 \frac{(nm)}{(cm)},$$

Typically, Raman spectroscopy is performed in the range 200-4000 $cm^{-1}$. A typical excitation wavelength may be 785 nm or 514 nm, however the selection of wavelength may be governed by a number of considerations, including the avoidance of excitation of fluorescence in the sample.

Typical devices that produce interferograms are usually variants of the Michelson interferometer and generally have moving parts that allow small changes to be introduced in the optical path length between beams of light. An energy beam may be divided into two and beams which travel different optical paths which may be subsequently recombined in a common region where interference occurs. Since a single wavelength would result in a detected intensity that varies periodically with the optical path length, these variations are called fringes. A simplified example of a prior art Michelson interferometer is shown in FIG. 1.

An interferometer operates, typically by splitting energy from a single source into two beams, and causing one of the beams travel a different physical distance than the other. When the two beams are brought together again, the phase difference between the beams results in an interference pattern comprised of a series of alternating light and dark fringes, depending on the energy wavelength and the difference in path length, resulting in a variation of detected intensity which is also dependent on the overall spectral characteristics of the energy within the passband of the instrument.

In this example, a Michelson interferometer 10 may comprise four "arms". The first arm is a source of optical energy 15, the second arm contains a stationary reflector 20, the third arm contains a movable reflector 25, and the fourth arm leads to an optical power detector 30, such as a photodetector. At the intersection of the four arms an optical beamsplitter 35 is disposed so as to transmit half of the energy impinging thereon and to reflect the other half of the energy. As a result, the energy transmitted by the beamsplitter strikes the fixed reflector 20, and the light reflected by the beamsplitter strikes the movable reflector 25. After reflecting off their respective reflector, the two energy beams recombine at the beamsplitter 35, and then exit along the fourth arm to the energy detector 30. In this configuration fifty percent of the light is lost prior to reaching the detector.

In a Michelson interferometer, a varying path difference between the two beams may be introduced by translating the movable reflector towards and away from the beamsplitter. This path difference may be expressed as a phase difference, where the phase difference is proportional to the path difference and inversely proportional to the wavelength of the energy. When the beams that have reflected off the fixed and movable reflectors recombine at the beamsplitter are in phase, an intense beam leaves the interferometer and impinges on the detector 30 as a result of constructive interference. When the fixed and movable reflector beams are recombined at the beamsplitter so that the beams are out of phase, little energy leaves the interferometer as there is destructive interference. The beam intensity measured by the detector 30 represents the contribution of all the energy from all of the wavelengths that are present. When the reflector 25 is moved so as to change the difference in path lengths of the beam components, the variation of the beam intensity with path difference is termed an interferogram.

Considering the interferogram to be related to the time-domain behavior of the signal resulting from the path length change, the interferogram has been recognized as the Fourier transform pair of the frequency spectrum of the energy producing the temporal pattern.

Modern digital signal processing technology enables rapid and precise determination of the corresponding frequency spectrum, including the amplitudes of the frequency components, from a time series. Such processing is generally performed by an algorithm known as a Fast Fourier Transform (FFT), although other spectral processing algorithms such as a DFT (discrete Fourier Transform) or Multiple Signal Classification may be used as well. The interferogram may be appodized (weighted) so as to minimize the effects of data truncation, as is known in the signal processing art.

The Michelson interferometer uses a beamsplitter, and a moving reflector. Changes in the alignment of the beamsplitter, and non-uniformities in the movement of the reflector contribute to errors in measurement and repeatability.

SUMMARY

A spectrometer is disclosed, including a diffraction grating comprising a first stairstep grating having a positive slope with respect to a base thereof, and a second stairstep grating having a negative slope with respect to the base thereof; a collimator disposed in an externally incident energy beam to direct the collimated beam to the diffraction grating at an off normal angle to the base of thereof; and a detector having a plurality of detection areas, the detector disposed so as to intercept energy specularly reflected by the diffraction grating. The first stairstep grating and the second stairstep grating may be interdigitated and have a common base.

A slit is disposed between the diffraction grating and the detector so as to select a zeroth-order reflection from the diffraction grating. The detector may be a photosensitive circuit, such as a charge coupled device (CCD) or other equivalent device such as a digital camera and the photosensitive elements may be disposed in a one-dimensional or two-dimensional array. The detected signal is input to a processor configured to perform a one- or two-dimensional Fourier transform of the detected signals. The Fourier transformed data may be compared with stored patterns to identify known substance types, and the results output in textual or visual form. The data may also be transmitted to another device for further analysis and reporting.

A lens, a mirror, or the like may be disposed in the optical path between the coherent light scattered by the sample and the detector so as form a compact optical path and to image the scattered light on a plane of the detector.

The spectrometer may include a coherent optical source, which may be a semiconductor laser or other laser whose energy is directed to illuminate a sample to be analyzed. The optical chain may include an edge filter selected to reflect energy at a wavelength of the coherent optical source, and to pass energy at at least a wavelength band having either a higher wavelength or a lower wavelength with respect to the coherent optical source.

In an aspect, the components of the spectrometer may be fixedly arranged with respect to each other.

In an aspect, the spectrometer may be housed in an apparatus containing camera to obtain an image a region that includes the region illuminate by the coherent optical source. The apparatus may interact with a position determining system or navigation system such that the physical location of the area being analyzed may be determined.

DESCRIPTION

Exemplary embodiments may be better understood with reference to the drawings, but these examples are not intended to be of a limiting nature. Like numbered elements in the same or different drawings perform equivalent functions. When a specific feature, structure, or characteristic is described in connection with an example, it will be understood that one skilled in the art may effect such feature, structure, or characteristic in connection with other examples, whether or not explicitly stated herein.

Embodiments of this invention may be implemented in hardware, firmware, software, or any combination thereof, and may include instructions stored on a machine-readable medium, which may be read and executed by one or more processors.

Figure 1:
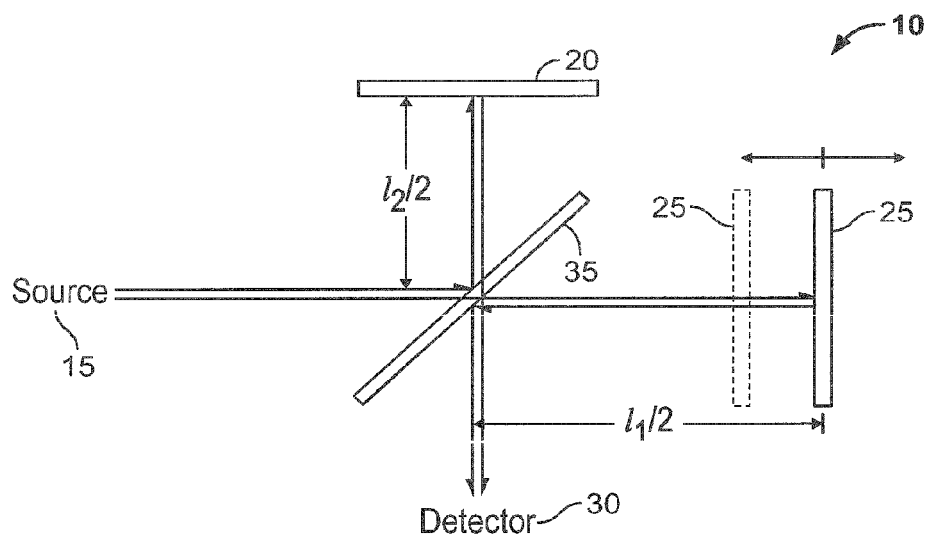
FIG. 1 is a plan view representation of a Michelson interferometer.
Figure 2:
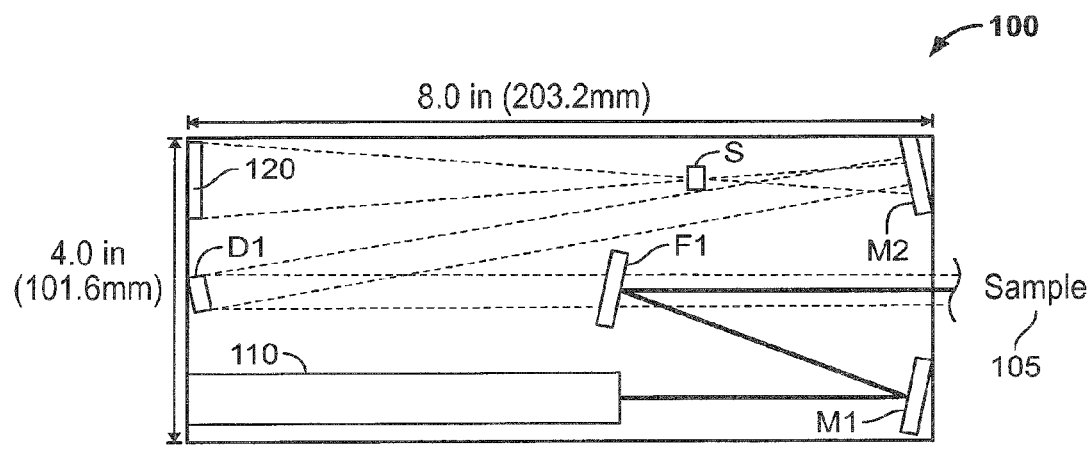
FIG. 2 is a plan view of a compact spectrometer incorporating a coherent energy source, a fixed interferometer grating and an energy detector.

FIG. 2 shows a conceptual design of a spectrometer 100 which may be used for Raman scattering or other spectral measurements. Collimated light from a laser 110 (collimator not shown), which may be a laser diode or similar device, may be directed by a mirror M1 to be reflected by an edge filter F1 so as to exit the device and irradiate a specimen 105 to be evaluated. A lens (not shown) may be disposed at the exit aperture of the spectrometer so as to collect the light energy scattered from the specimen 105 and direct the light through the edge filter F1 so as to impinge on the interferometer element D1.

Apart from elastically scattered light energy, which is unchanged in frequency from the incident light, inelastic scattering results in wavelength-shifted (Raman) emissions that represent the Stokes and anti-Stokes response of a particular sample of material. These emissions are shifted in wavelength from the irradiating wavelength, and a portion of the emissions is directed back along the direction of the light emitted from the aperture of the spectrometer 100. The detailed spectral characteristics of the Raman-scattered light are of interest, as the spectral characteristics may be used to identify different material types, including composite material types.

The edge filter F1 may be an optical device having a passband and a stopband, wherein the transition between the passband and the stopband is relatively sharp. Light impinging on the edge filter F1 in the passband may pass through the filter with little attenuation, whereas light impinging on the edge filter in the stopband is essentially totally blocked. Here, the characteristics of the edge filter F1 may be chosen such that the excitation light wavelength is in the stopband and the filter reflects the excitation light from the edge filter F1, directed towards the specimen 105. Light returning from the specimen 105 is comprised of the unshifted (elastically scattered) laser light and the Raman emissions (inelastically scattered light) that are shifted in wavelength from the laser light. The unshifted laser light returning from the specimen 105 is again reflected from the filter F1, and may be directed towards an absorbing region (not shown) within the spectrometer so as to be substantially attenuated. One of the group of Stokes lines or anti-Stokes lines of the Raman spectrum may be transmitted through the filter F1, depending on whether the filter F1 is of the long-wave-pass or the short-wave-pass design, so as to impinge on a reflective element D1, which may have dispersive characteristics.

The Raman scattered light may then be reflected off of the dispersive element D1 which separates the light into different spectral components. The dispersed light is then reflected off of a mirror M2 which may be a focusing mirror, through an aperture S and is then be detected by a camera 110, which may be a charge coupled device (CCD). Other components such as focusing lenses or mirror may be used, but are not shown for simplicity.

In an example, the CCD may be a one or two-dimensional array of light sensitive elements that are used to record the one of two-dimensional spatial distribution of the light impinging thereon.

Figure 3:
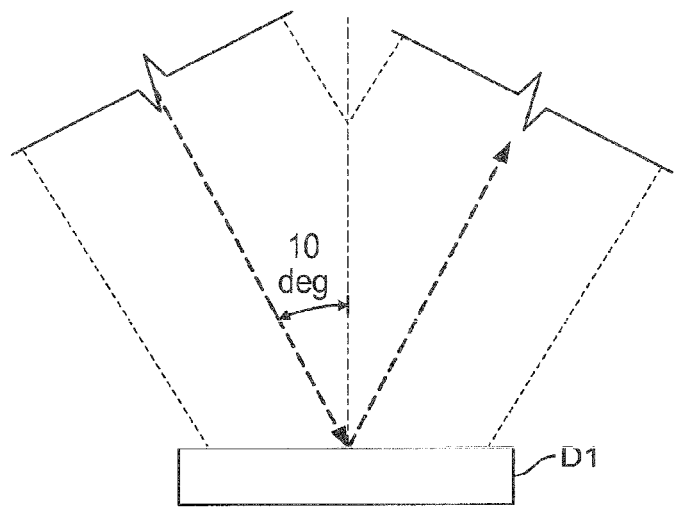
FIG. 3 illustrates a grating (D1) with an off-normal incidence energy source.
Figure 4:
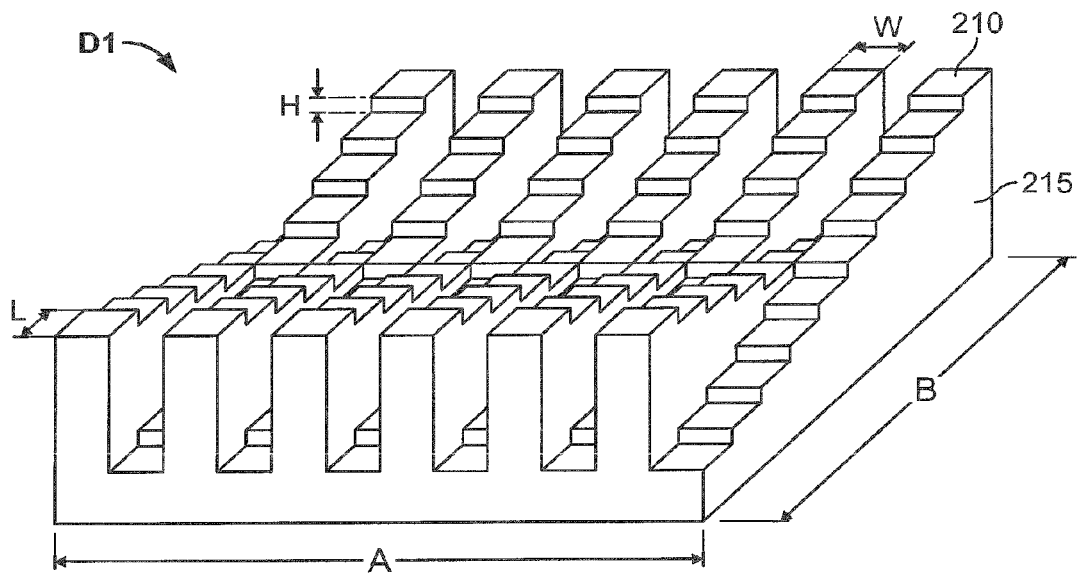
FIG. 4 illustrates a grating having interdigitated staircase elements.

FIG. 3 shows the Raman-scattered light incident on a diffraction element D1 which may be a reflecting staircase grating as shown in FIG. 4. In this example, the plane of the base of the diffraction element D1 is oriented at an angle of about 10° to the incoming light as shown in FIG. 2 so as to direct the light onto the mirror M2 and to avoid the edge filter F1 or other internal components of the device. The individual steps 210 of the staircase element 215 create a multitude of reflected beams having different optical path lengths when beams have propagated so as to be reflected from the focusing mirror M2 to converge at the aperture S. Each individual beam is a wave-front and the individual wave-fronts overlap on the focal plane where the CCD 110 is located. As is typical of grating-type reflective elements, various orders of dispersed energy results. In this instance the aperture S is used to select zeroth-order rays, while blocking the higher order dispersion products.

FIG. 4 shows an example of alternating or interleaved staircase elements having opposite slopes, where the base of the structure is oriented at an angle to the incoming optical signal as shown in FIG. 2.

In the example of FIG. 4, the interdigitated staircase elements may be comprised of steps, each step having, for example, a height (rise) H and length (run) L of 5 microns, and width W of 50 microns. So, the periodicity of the structure in the direction perpendicular to the staircase elements (A direction) would be 100 microns. Each of the interdigitated staircases 215 may comprise, for example, 2000 individual steps (a substantially fewer number of steps are shown for clarity), so that the length of the base of the staircase is about 1 cm (B direction). The height of the top of the staircase 215 above the base is also about 1 cm.

Each staircase step element 210 has a length parallel L to the base of the structure. An elemental slice of the light beam oriented perpendicular to the plane of the staircase element and illuminating pairs of steps of the staircases may be considered as an element of the grating with a difference in path length of twice the height difference H of the steps. The plane of base of the diffraction element D1 is oriented at an angle to the incoming light beam. The steps 210 of both of the staircase elements 215, being parallel to the base, are oriented at the same spatial angle as the base.

Adjacent stairsteps 215 have slopes of opposite sign, so that the difference in vertical elevation therebetween increases by twice the rise of each individual stairstep element for every increment of run along the stairstep. This is the situation where the rise and the run have the same linear dimension. However other values of rise and run may be used and result in different stairstep slopes. The stairstep width dimension may differ from each of the stairstep rise and run The arrangement is similar to a lamellar grating, where the optical path between a sloped element and a reflection from the base length would vary continuously along the length of the reflecting surface. The specular reflection angle of a conventional lamellar grating is small, perhaps 5 degrees. However the reflection of energy from the base and from the sloped surface would be at different angles for the specular (zeroth-order) case. As such, there is a practical limit on the tilt angle of the sloped element of a conventional lamellar grating. This places a corresponding limit on the maximum total path length difference which can be created by the lamellar grating. Since the resolution of a spectrometer device of this type depends on the inverse of the maximum path length difference between the interfering energy beams, the resolution of a conventional lamellar grating is poor.

The plane of the steps in the staircase of FIG. 4 are disposed substantially parallel to the base, and when the base is oriented at an angle to the incoming beam as shown in FIG. 2, all of the specularly reflected energy is directed at a same reflection angle. In this instance, where the angle of incidence of the optical energy is 10° with respect to orthogonal incidence, the specularly reflected components (zeroth order dispersion) from each of the adjacent stairstep elements is −10°, even though the overall slope of the stairstep 215 is ±45° with respect to the base. As such, the maximum path length difference that may be achieved is substantially greater than for a conventional lamellar grating, and the resolution is correspondingly better.

As described above, for the zeroth-order rays, wavelength-related dispersion does not occur. Rather, all of the wavelengths are reflected at the same angle, as is typical of specular reflection. The specific reflection angle is determined by the overall orientation of the structure with respect to the incoming optical beam. But, the stairstep arrangement of the reflector causes the light reflected from closely-spaced portions of the stairstep structure 215 to have differing physical optical path lengths at the camera 120 or detector. So, the phase difference between components of the reflected light at the camera 120 depends on the wavelength of the light.

Figure 5:
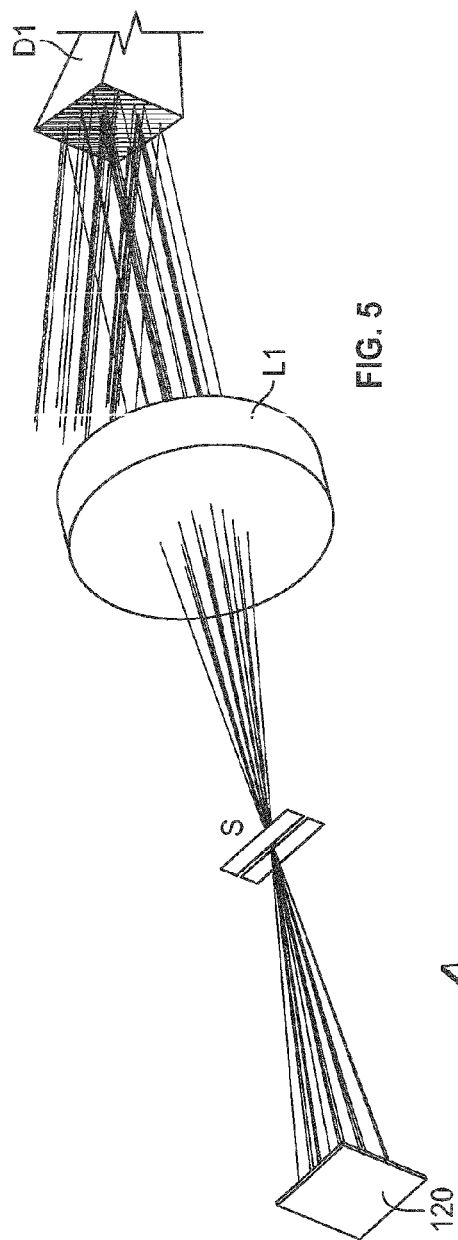
FIG. 5 illustrates the path of the dispersed energy from the grating being selected by a slit before being detected at the image plane.

An aperture or slit S is disposed at the focal plane of the zeroth-order component so that the higher-order dispersion products are blocked. The light rays resulting from specular reflection of the incoming light from the stairstep dispersive element, that have been selected by the aperture S, impinge on the detector array 120 as shown in FIG. 5. In this figure, a lens L1 rather than a spherical mirror M2 is used to focus the light received from dispersion element D1. The choice between a mirror and a lens may be dependent on the geometrical arrangement of the components, and whether any chromatic dispersion of the lens may be acceptable. A planar mirror, not shown in FIG. 5, may be used to fold the optical path as shown in FIG. 2.

An camera 120, which may be an energy detector array such as a charge coupled device (CCD), may be disposed at a suitable distance from the slit S so that the selected zeroth-order dispersion (reflection) products fall thereon, and the spatial properties of the interferogram are determined. In this example, a CCD having a dimensionality of 1280×1024 pixels, each pixel having a dimension of 7 microns was used for experimental purposes. Each pixel may be associate with an individual detector element of the CCD disposed in a two dimensional array.

When the light energy impinges on an individual detector element of the CCD, the differing optical wavelengths and path lengths associated with the stairstep properties of the reflector result in an interference result. Where the detector is a plurality of detector elements, such as may be found in a charge coupled device (CCD), or other detector array an interference pattern is created by the action of detecting the energy as a function of distance along the CCD x-y plane. This two-dimensional interference pattern is an interferogram which is characteristic of the wavelengths and amplitudes of the components of the light present. Such a pattern is an autocorrelation function and has a well-known Fourier-transform-pair relationship with the frequency spectrum of the light causing the interference pattern. The optical resolution depends on the total optical path length difference which is four times the total step height (the dispersive device D1 height).

Figure 6:
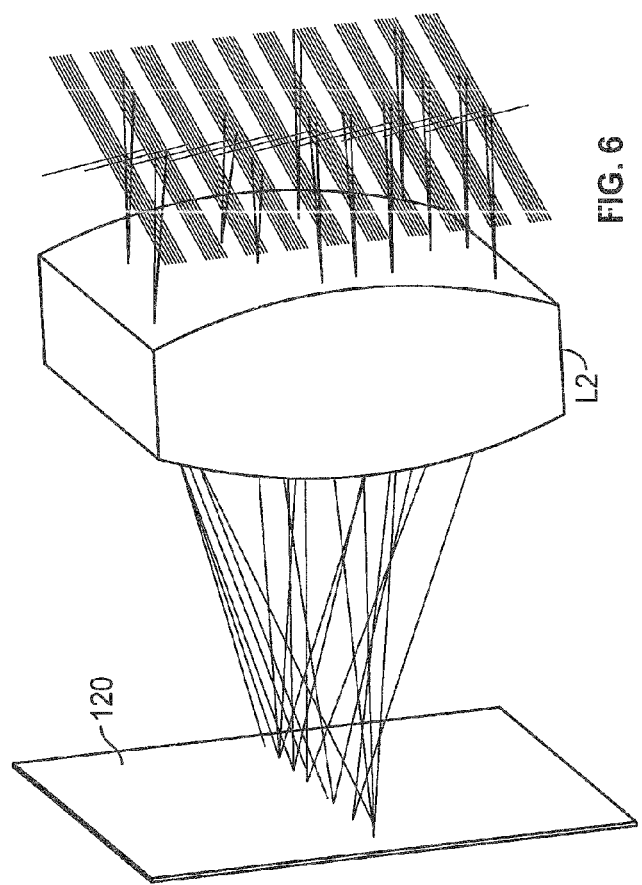
FIG. 6 illustrates the use of a cylindrical lens interposed between the slit S and the image plane so as to collapse the 2-dimensional Fourier spectrum to 1 spatial dimension.

In this example, the energy in the image plane is spread in two dimensions, so that the interferogram is a two-dimensional pattern and is processed by a two-dimensional Fourier transform. Alternatively, a cylindrical lens L2 may be disposed between the slit S and detector array at the image plane, as shown in FIG. 6 so as to focus the energy into a linear pattern so that a one-dimensional Fourier transform may be used. This is a design choice which may be made depending on the specific performance attributes desired.

To evaluate an example of a dispersive element D1, ZEMAX simulation software (Radiant ZEMAX LLC, Bellevue, Wash. 98004 USA) was used for a 10 mm×10 mm×10 mm element comprising 2000 steps in the ramp, each step having a height (rise) H and length (run) L of 5 microns, and width W of 50 microns. With a scattered light incidence angle of 10° to the normal of the grating surface, a resolution greater than 0.025 nm at incident wavelengths near 500 nm was obtained. The use of an interlaced grating avoids a beam splitter, allowing more light to reach the detector. Moreover, the physical relationships between the interleaved portions of the grating are fixed at the time of manufacture and do not require further adjustment or calibration.

When the angle of incidence on the grating is 10° (effectively normal incidence to the run and width dimensions thereof) and the step height is equal to the step length, 82 percent of the incoming light is reflected from the surface of the device as compared with a configuration using a beam splitter where only 25 to 50 percent of the light reaches the detector.

The configuration of the dispersion element D1, described above, permits a spectral resolution comparable to that of a bench-top laboratory system. For example, the resolution of a Y2 meter Czerny-Turner monochromator utilizing a 2400 l/mm grating with a central wavelength of 500 nm and a slit width of 50 microns is 0.06 nm, with a bandpass of 0.037 nm. This comparison device is a scanning-type interferometer and essentially one-wavelength-resolution-element-at-a-time is measured and the intensity values of the interferogram elements are obtained sequentially. Mechanical movement of the grating is required to cover an adequate spectral range, whereas no mechanical movement is required for the configuration in FIG. 2.

In another aspect, the excitation light energy may be delivered to the sample 105 by a separate path from that on which the scattered light may be received by the spectrometer. The light may be delivered by free-space optics, fiber optics, or a combination of the techniques. Further, a plurality of energy sources may be used. The scattered light may be returned to the spectrometer by a light pipe, an imaging lens or the like, such that mirror M1 may be eliminated, and the filter F1 used as a bandstop filter to suppress the excitation light that is elastically scattered back to the spectrometer.

Other spectrometer uses may not involve the illumination of a specimen by an optical energy source associated with the spectrometer. An emission spectrum or scattering spectrum of an object may be measured by collecting light radiated or reradiated from the object and, using the dispersive element D1, the slit S and the detector 120 so as to produce an interferogram of the collected light.

The type of spectrometer described herein does not have any moving parts associated with the optical paths, and the orientation of the elements of the optical chain is fixed at the time of manufacture. This approach results in a device having lower sensitivity to environmental effects, including shock and thermal effects, a high efficiency in collecting and detecting the energy to be analyzed, and the ability to process all of the spectral bandwidth simultaneously using a Fourier transform processing technique. By collecting all of the of the interferogram pattern simultaneously, the temporal response time of the measurement is substantially improved. Many of the signal processing techniques that have been developed for spectral-domain and time-domain processing of electrical signals and images may be used analogously here so as to improve signal-to-noise ratio, correct aberrations in the optical device and other such features as are known in the art.

The selection of the wavelength of the exciting energy depends on the specific substances to be investigated and may range over the entire visible and near visible spectrum, compatible with the selection of the optical components of the spectrometer. Tests have been made at 408 nm and solid state lasers at about 514, 785 and 1060 nm would also be useful The particular dimensions of the grating may be influenced also by the choice of fabrication method. When fabricating extremely small structural elements, the manufacturing technology selected may be constrained by currently available technology. However, nothing herein should be interpreted to require that the grating be fabricated by a particular technical approach.

Figure 7:
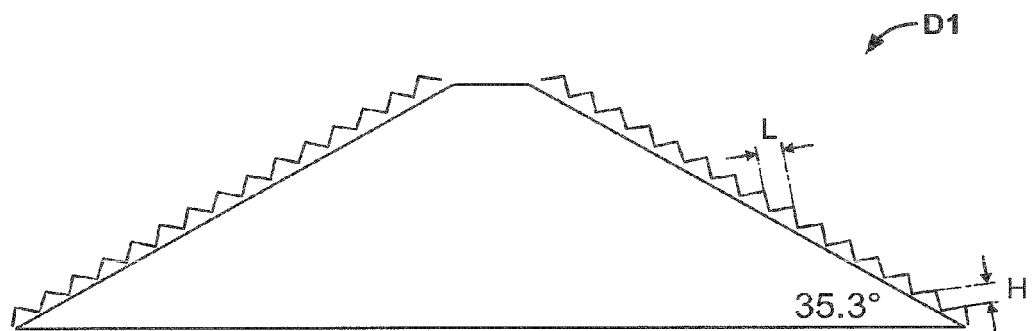
FIG. 7 illustrates a stepped grating configured to be suitable for manufacturing by a hot embossing process.
Figure 8:
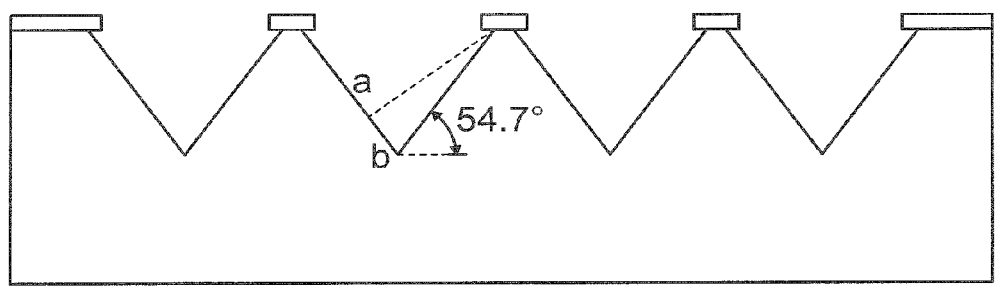
FIG. 8 illustrates the fabrication of a blazed grating suitable for hot embossing a grating.

An example of a pyramidal form diffractive element which may be manufactured by hot embossing is shown in FIG. 7. Here the stairstep is inclined at an angle of 35.3° to the base. Such a diffractive element may be fabricated by a hot embossing process using a blazed grating mold in silicon. The mold itself may be fabricated from a silicon substrate that has been TMAH (tetramethyl ammonium hydroxide) etched along crystal planes. The spacing of the grooves is determined by a photoresist or other techniques as shown in FIG. 8. The combination of the plane angle of the mold (54.7°) and the slope of the pyramid that is being embossed (35.3°) provides for surfaces surface of the grating that are perpendicular to the incident light energy for both slopes of the stairstep.

The grating body may be any material suitable for hot embossing, which may then be provided with suitable reflecting surface coating.

In another design example, the underlying theory is outlined and then applied to measurement of a Raman spectrum. The design for other wavelengths and applications would follow a similar path, as would be understood by a person of skill in the art having the benefit of the present description.

Assume that the spectrum that is to be measured has a minimum wavelength $\lambda_{min}$, and a maximum wavelength $\lambda_{max}$. The dispersed spectrum is to be imaged onto CCD or other detection device 120, which we shall generically call a "camera." In a one dimensional situation, the camera may be characterized as having a resolution of $N_{xpix}$ along an X axis. In a two-dimensional case, the resolution along the Y axis is also considered.

With reference to FIG. 4, the step height h, number of steps $N_{step}$, step depth d and step width w are the design parameters to be considered. If the step height h is an integer number (M) of half wavelengths at an optical wavelength, then constructive interference occurs and, at the minimum design wavelength $\lambda_{min}$ the step height h for normal incidence is:

$$h = M\lambda_{min}/2 \ (M=1,2,3,4,\ldots)$$

For wavelengths other than the minimum wavelength $$\lambda = \delta\lambda + \lambda_{min}$$

and optical path difference from the step is $2M\delta\lambda/2 = M\delta\lambda$. For one slope of the stepped grating the total optical path difference is $\delta\lambda MN_{step}$. An interference line occurs when the increment of optical path is one wavelength, so that $$\delta\lambda/\lambda = 1/(MN_{step})$$

along a single slope of the stepped grating step of the stairstep. The resolution is doubled if the gratings are interleaved as shown in FIG. 4.

Figure 9:
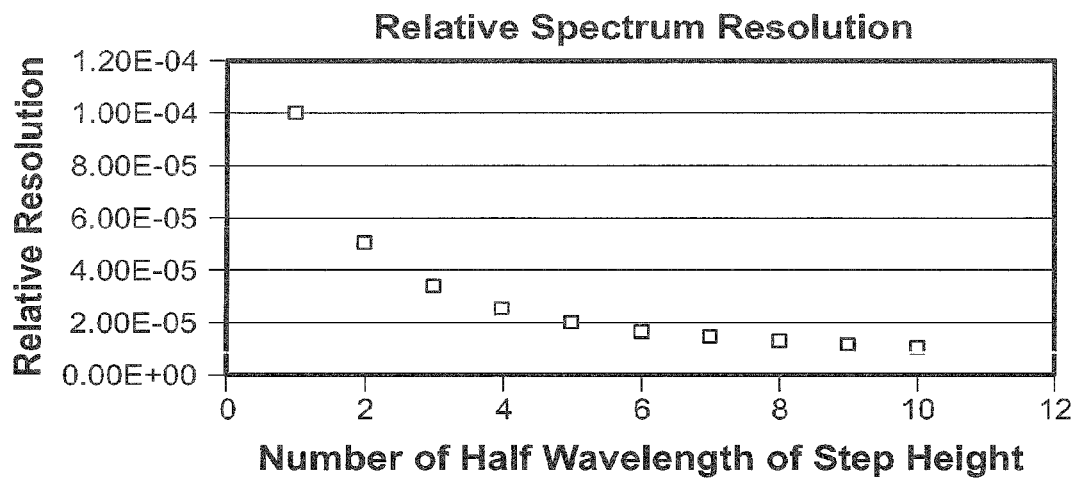
FIG. 9 is a graph of the relative spectrum resolution as a function of the number of half wavelengths of step height, if there are 5000 steps.

In an example, consider a stairstep grating with 5000 steps. The resolution is a function of the number of half wavelengths per height step, and is shown in FIG. 9.

Where the spectral range is imaged onto the full width of the camera detection element, the resolution of the camera, in pixels, should be at least twice the number of interference lines $N_{max}$, in accordance with the Nyquist sampling theorem:

$$\lambda_{max} - \lambda_{min})/\lambda_{min} = \delta\lambda N_{max}/\lambda_{min} = N_{max}/(2MN_{step})$$

Figure 10:
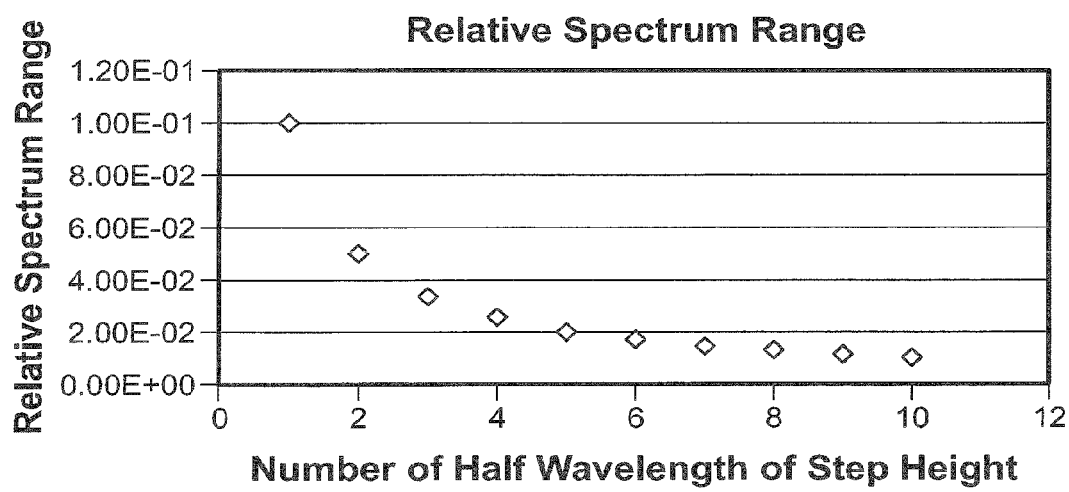
FIG. 10 is a graph of the relative spectrum range as a function of the number of half wavelengths of step height, if there are 5000 steps, and camera can identify 1000 lines.

In an example where the grating has 5000 steps and the camera has 2000 pixels, FIG. 10 shows the relationship of the relative wavelength range to the number of half wavelengths M of step height h: In practice, the resolution in pixels should greater than about twice the Nyquist criteria.

An interlaced grating for measuring the Raman spectrum over a wave number range of 800 cm-1 from 1000 cm$^{-1}$ to 1800 cm$^{-1}$, with a spectrum resolution 0.4 Å may use a camera with, for example, 2560 pixel resolution so as to identify at least 1000 spectral lines of the spectra. The excitation laser may be a 408 nm device (wave number 1/408 nm=2.4509804×10$^{-3}$ nm$^{-1}$=24509.804 cm$^{-1}$). The maximum wave-number is 24509.8−1000=23509.804 cm$^{-1}$ and correspondent wavelength is 0.4253545 um=4253.545 Å; the minimum wave number is 24509.8−1800=22709.804 cm$^{-1}$ and the corresponding wavelength is 0.44033845 um=4403.3845 Å; and, the central wave number is 24509.8−1400=23109.804 cm$^{-1}$, or a wavelength 0.43271678 um.

In this example, the step height is 2 times (M=4) of the minimum wavelength 4253.545 Å, that is 0.850709 um. If spectral energy to be measured is incident at 10° with respect to normal incidence, the effective height should be divided by cos(10°), yielding h=0.86383256 um. If Si was used to fabricate the stairstep grating, the Si line interval would be 0.86383256/sin(54.7°)=1.0584399 um. The Si beam length is 1.0584399 um ×3600=3.810383 mm for 3600 steps.

For a wavelength equal to the minimum wavelength, a 1 Å increase in wavelength results in a total of 4×3600 Å=1.44 um optical path difference, that is 1.44 um/0.425354 um=3 interference lines for a single grating (resolution of about 0.4 Å), but an interlaced grating would have 6 interference lines. A 150 Å spectrum range, dispersed by a interleaved grating would have about 1000 lines, and a 2560 pixel camera would work satisfactorily.

The resolution may be increased by increasing the step height, as has been noted previously; however, this results in a reduction in spectral range, for the same resolution camera. The spectral range may be doubled by tilting one of the stairstep gratings of an interlaced grating of the pair by about 0.01° about the X axis. The resulting two dimensional interference pattern for wavelengths longer than 4253.545 Å will rotate clockwise, while the interference pattern for wavelengths shorter than 4253.545 Å will rotate counter clockwise. By setting the center wavelength to 0.43271678 um, the spectral range can be doubled.

Figure 11:
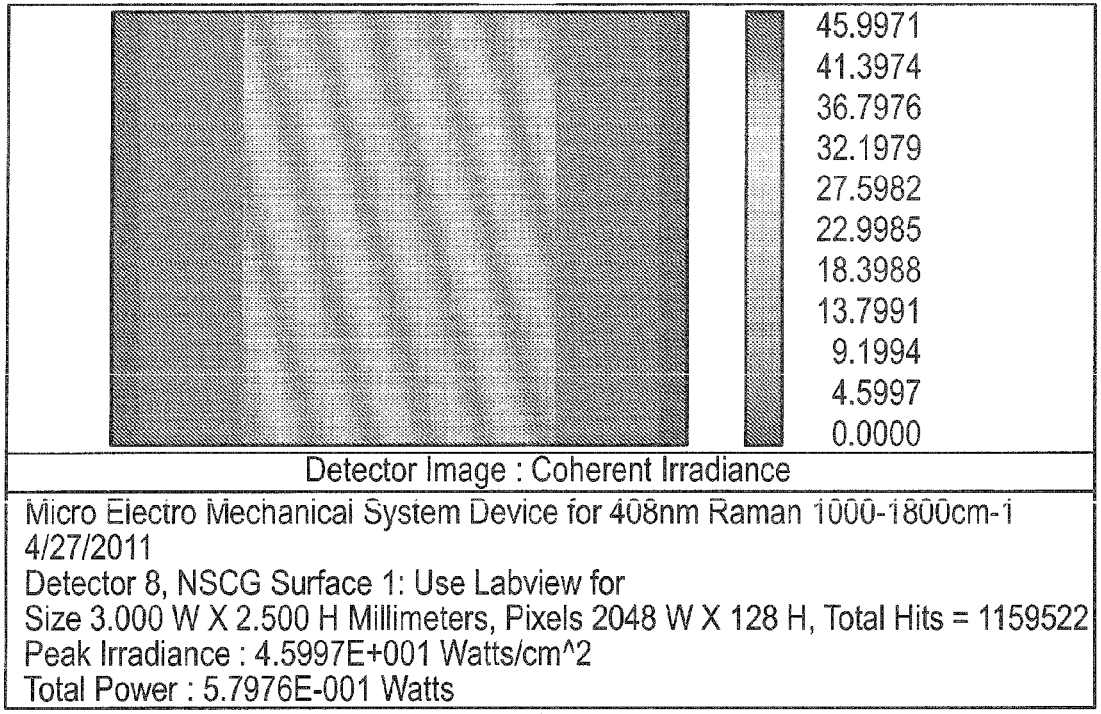
FIG. 11 is an intensity simulation for wavelength 4252.545 Å and a tilt angle of 0.01 degree.
Figure 12:
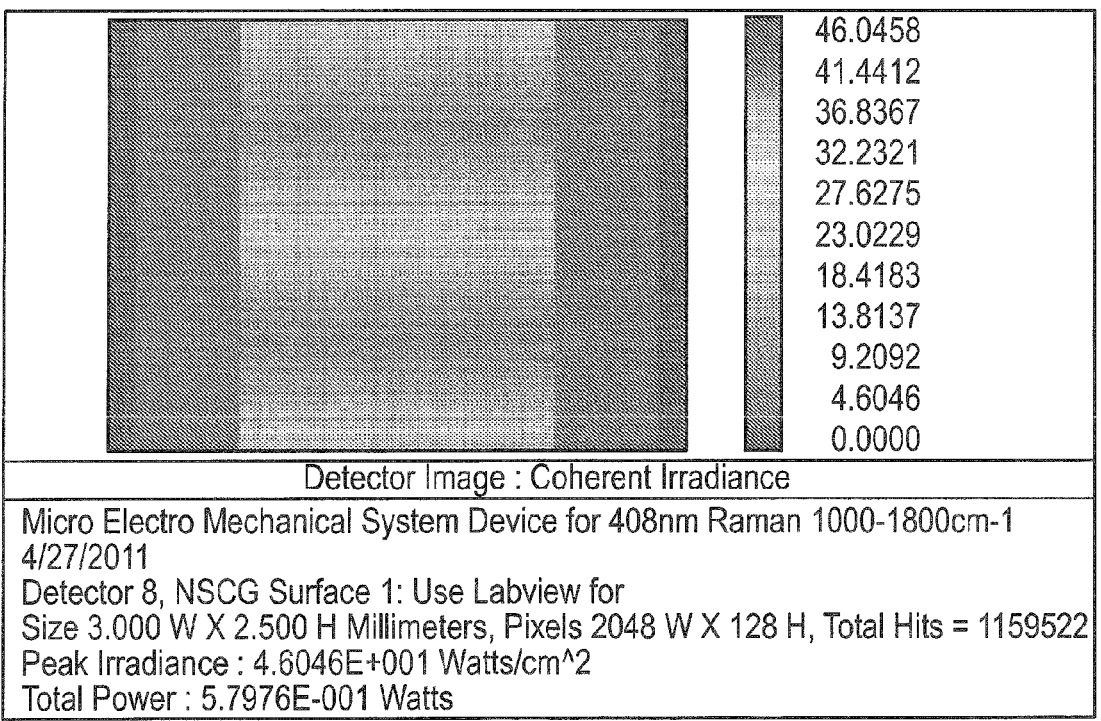
FIG. 12 is an intensity simulation for wavelength 4253.545 Å and a tilt angle is 0.01 degree.
Figure 13:
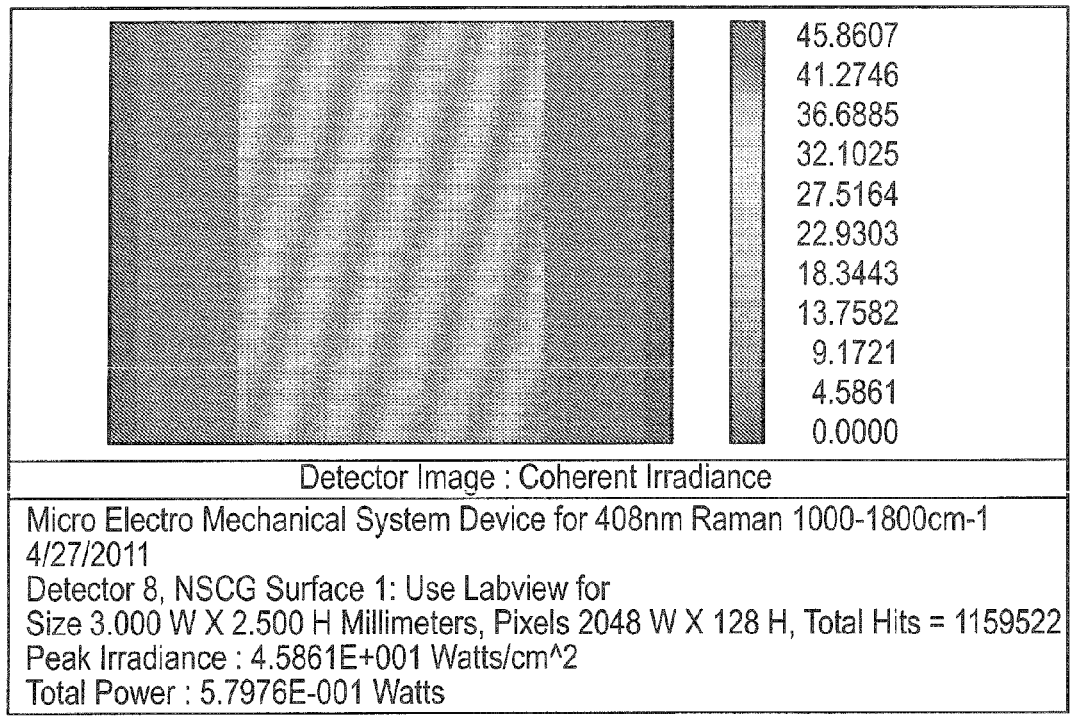
FIG. 13 is an intensity simulation for wavelength 4254.545 Å. Tilt angle is 0.01 degree.

The ZMAX simulation program was used to compute interferograms for the tilted grating arrangement for 4252.545 Å, 4253.545 Å and 4254.545 Å and the results shown in FIGS. 11-13. The step width is 25 um, and there are 50 pairs of interlaced gratings in the overall structure.

Figure 14:
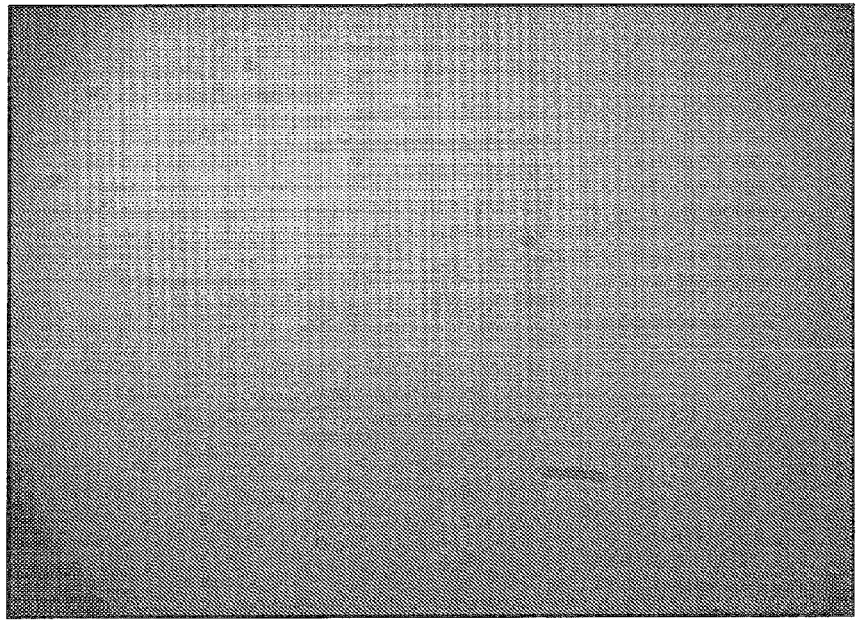
FIG. 14. Is a photograph of the observed interference pattern for Hg light, the wavelengths are 546.08 nm, 576.96 nm and 579.07 nm. The camera resolution is 1280×1024, one group of grating has step height of 2500 Å or 250 nm; while the other group grating is a mirror.

FIG. 14 shows the observed interference pattern for Hg light, the wavelengths are 546.08 nm, 576.96 nm and 579.07 nm. The camera resolution is 1280×1024. One group of grating has step height of 2500 Å or 250 nm; while the other group grating is a mirror. The main interference pattern is from the bright green line, 546.08 nm. From the Fourier transform pattern, one can see the other two lines. This simple experiment illustrates the concept the design.

Figure 15:
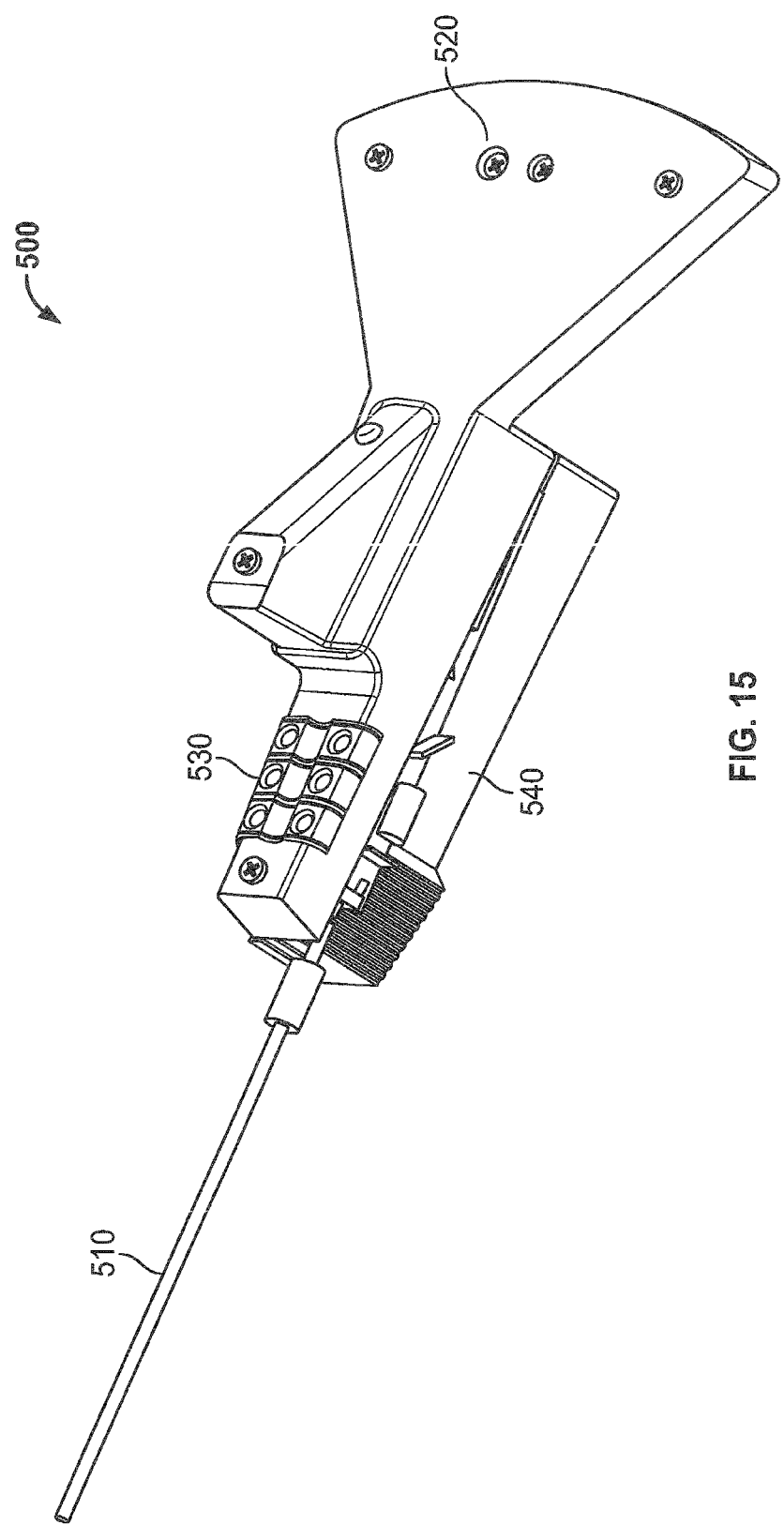
FIG. 15 is a perspective view of an example of the use of a stepped grating interferometer in a hand held device having local navigation capability; and, FIG. 16 is a cutaway view of FIG. 15 showing a conceptual location of the spectrometer components.
Figure 16:
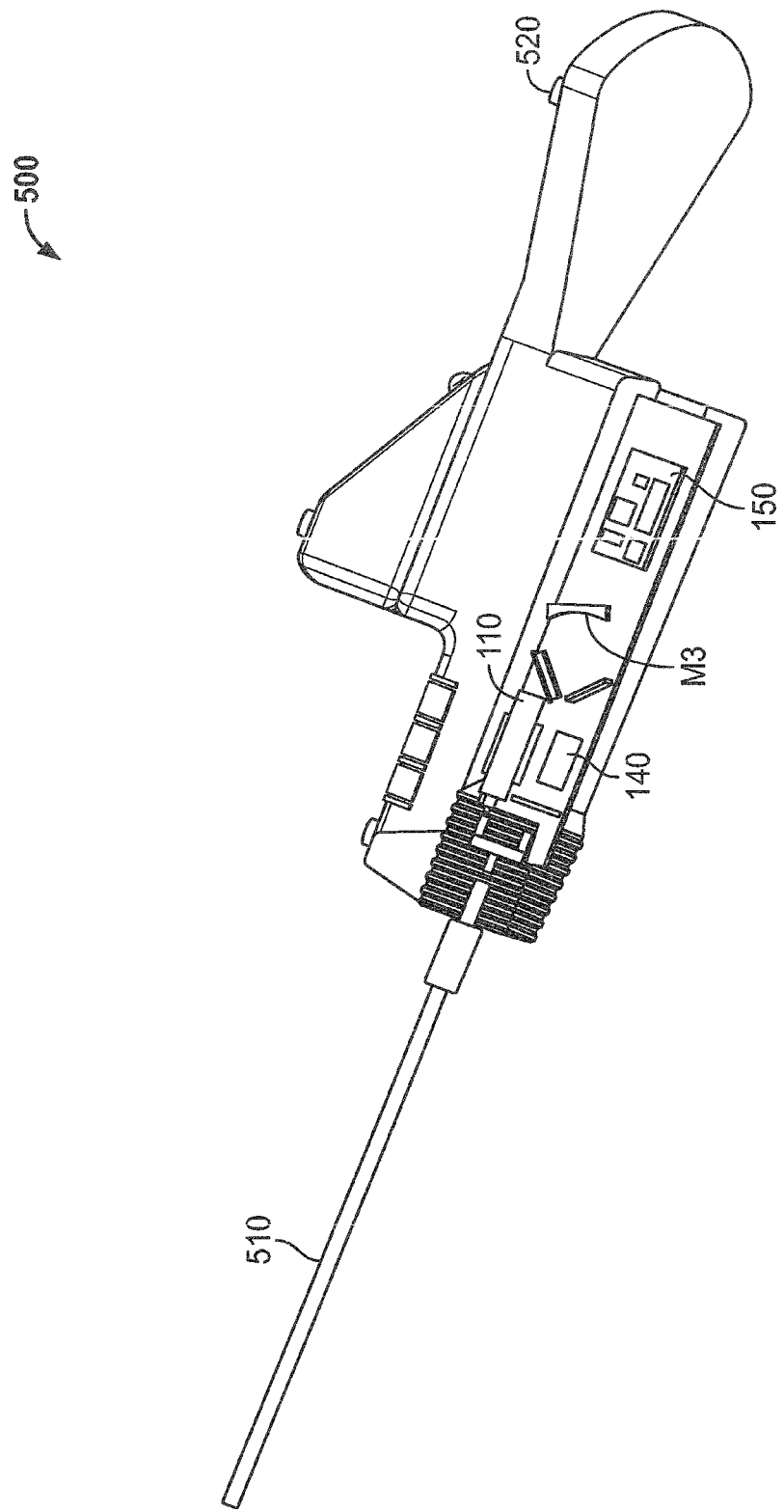

A small, rugged spectrometer may have a variety of applications, in Raman spectrometry and in other spectrometric applications. For example, a Raman spectrometer may be packaged in a small hand held device, such as is shown in FIG. 15 and FIG. 16. This is an example of a housing of a Stryker ENT camera system having a navigation capability in which the Raman spectrometer may also be housed. The system uses photodiodes 520 to track the location and orientation of the device, and the field of view in real time for surgical applications. FIG. 15 shows an external view of a concept of the portable Raman spectrometer. The tracking diodes are used in conjunction with an external sensor system (not shown) to locate the probe 510 with respect to another object. Other orientation systems, which may use magnetic or electromagnetic sensors are also known and may be used. Various functions of the probe may be controlled by a group of buttons 530, and the results displayed on a screen (not shown) that is part of the apparatus 500, or on a separate display.

FIG. 16 illustrates a different perspective view of the apparatus where a portion of the housing 540 is removed so as to show possible locations of the spectrometer components, including an electronics card 150 which may include a processor. The processor may execute a stored program to configure the processor to perform a Fourier transform of the detected optical data, to compare the transformed data with Raman spectral signatures of substances of interest, and to report the results. Alternatively, the data may be transmitted by wired or wireless means to an external processor which may perform some of all of the processing of the detected optical data.

It is known that normal and abnormal tissues of the same type exhibit different Raman spectra. Intra-operatively imaging an in-vivo tissue may assist the surgeon in more precisely delimiting the area to be excised during the procedure. Such a tool may permit the surgeon to more definitively ascertain whether the entire affected area has been removed. In any event, a preliminary diagnosis may be made without waiting for laboratory results.

A conventional CCD camera apparatus, as is ordinarily used by the current commercial product may be supplemented by the Raman spectrometer described herein, or a separate Raman spectrometer having the same or similar navigation capabilities may be used. The Raman spectrometer may be configured to have a smaller field of view than that of the visible camera, and the spectrometer probe manually or automatically scanned over the area to be investigated. The resultant visible and spectrometer results may be combined for visualization by known image processing techniques. When the Raman spectrometer results indicated abnormal tissue, by a specific characteristic Raman spectrum, the region may be indicated on the visible camera image by false color imaging.

Other device navigation systems which may use, optical, magnetic, acoustic or radio frequency positioning technology may be used. Alternatively, a configuration where the same device has both a camera and the Raman spectrometer may display a visual image, and the portion of the visual image being illuminated for the Raman spectrum may be indicated thereon. The result of the spectrum measurement may be displayed as a graph, or the spectrum may be compared with a library of spectra in the processor and the substances (s) which match the library spectrum may be indicated by a text or color. Since the entire spectrum is obtained simultaneously, the movement of the probe so as to manually or automatically scan an object may permit localization of a particular substance in a heterogeneous object or mixture.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

What is claimed is:

1. A spectrometer, comprising:
   a diffraction grating comprising a first stairstep grating having a positive slope with respect to a base thereof, and a second stairstep grating having a negative slope with respect to the base thereof;
   a collimator disposed in an externally incident energy beam to direct the collimated beam to the diffraction grating at an off normal angle to the base of thereof; and
   a detector having a plurality of detection areas, the detector disposed so as to intercept energy specularly reflected by the diffraction grating,
   wherein the diffraction grating and the detector are fixedly mounted with respect to each other.

2. The spectrometer of claim 1, wherein a slit is disposed between the diffraction grating and the detector.

3. The spectrometer of claim 2, wherein a reflector is disposed between the diffraction grating and the slit.

4. The spectrometer of claim 1, wherein a detection area is a photosensitive circuit and the detection areas are arranged as a linear array.

5. The spectrometer of claim 4, wherein energy detected by the detector is communication with a processor configured to perform a one-dimensional Fourier transform.

6. The spectrometer of claim 1, wherein a detection area is a photosensitive circuit and the detection areas are arranged as a two-dimensional array.

7. The spectrometer of claim 6, wherein energy detected by the detector in communication with a processor configured to perform a two-dimensional Fourier transform.

8. The spectrometer of claim 1, further comprising:
   a coherent optical source disposed so as to illuminate a sample to form the externally incident energy beam.

9. The spectrometer of claim 8, further comprising:
   an edge filter,
   wherein the edge filter is selected to reflect energy at a wavelength of the coherent optical source, and to pass energy at least a wavelength band having either a higher wavelength or a lower wavelength with respect to the coherent optical source.

10. The spectrometer of claim 9, further comprising a housing within which the spectrometer is mounted, the housing having an aperture to pass the energy to be detected.

11. The spectrometer of claim 10, wherein the orientation and location of the housing is determined by a navigation system.

12. The spectrometer of claim 3, wherein the reflector is planar.

13. The spectrometer of claim 3, wherein the reflector has an axially symmetric surface.

14. The spectrometer of claim 3, wherein the reflector has a cylindrical surface.

* * * * *